(12) United States Patent
Vivero et al.

(10) Patent No.: US 10,902,945 B2
(45) Date of Patent: Jan. 26, 2021

(54) DATA ANALYSIS MECHANISM FOR GENERATING STATISTICS, REPORTS AND MEASUREMENTS FOR HEALTHCARE DECISIONS

(71) Applicant: Amino, Inc., San Francisco, CA (US)

(72) Inventors: David A. Vivero, San Francisco, CA (US); Jorge A. Caballero, Menlo Park, CA (US); Abraham M. Othman, San Francisco, CA (US); Farid Jamshidian, South San Francisco, CA (US); Eithon Michael Galinato Cadag, Foster City, CA (US); Abhinav Chowdary Yarlagadda, San Francisco, CA (US); James Lyon Fingal, San Francisco, CA (US); Nicholas C. Dunkman, San Francisco, CA (US); Kunal Dhiren Shah, San Francisco, CA (US); Willard Kirk Strauser, Alameda, CA (US); Michael H. Lin, Saratoga, CA (US); Mary Audrey Hampden, Alameda, CA (US); Sumul Mahendra Shah, Alameda, CA (US); Rebecca Ackermann, San Francisco, CA (US)

(73) Assignee: Amino, Inc., San Francisco, CA (US)

( * ) Notice: Subject to any disclaimer, the term of this patent is extended or adjusted under 35 U.S.C. 154(b) by 1207 days.

(21) Appl. No.: 14/990,744

(22) Filed: Jan. 7, 2016

(65) Prior Publication Data
US 2016/0196398 A1    Jul. 7, 2016

Related U.S. Application Data

(60) Provisional application No. 62/100,890, filed on Jan. 7, 2015.

(51) Int. Cl.
*G16H 40/20* (2018.01)
*G06F 19/00* (2018.01)
(Continued)

(52) U.S. Cl.
CPC .......... *G16H 40/20* (2018.01); *G06F 19/324* (2013.01); *G06F 19/328* (2013.01);
(Continued)

(58) Field of Classification Search
CPC ............................................... G06Q 50/22–24
See application file for complete search history.

(56) References Cited

U.S. PATENT DOCUMENTS 6,418,433 B1    7/2002    Chakrabarti
2003/0158751 A1    8/2003    Suresh et al.
(Continued)

OTHER PUBLICATIONS

Qing T. Zeng, PhD, Tony Tse, PhD, Exploring and Developing Consumer Health Vocabularies, Journal of the American Medical Informatics Association, vol. 13, Issue 1, Jan. 2006, pp. 24-29, https://doi.org/10.1197/jamia.M1761 (Year: 2006).*
(Continued)

*Primary Examiner* — Robert A Sorey
(74) *Attorney, Agent, or Firm* — Perkins Coie LLP

(57) ABSTRACT

Disclosed are systems and techniques for providing a master health entity index and a data analysis mechanism designed for entity cohort discovery and entity profiling. The entity can be a healthcare facility that diagnoses or treats health conditions and diseases (e.g., hospital, clinic), individuals (e.g., providers, patients, caregivers), healthcare data (e.g., medical conditions, treatments, diagnostic studies, health outcomes), etc. For example, a data analysis mechanism may identify distinctive patient cohorts based on what happened to patients in a hospital and why the occurrence happened, glean insight from the activities of the distinctive (Continued)

patient cohorts, and assist with additional patients with the gleaned insight.

21 Claims, 19 Drawing Sheets

(51) Int. Cl.
*G16H 50/30* (2018.01)
*G16H 15/00* (2018.01)
*G06Q 10/06* (2012.01)

(52) U.S. Cl.
CPC ......... *G06Q 10/0635* (2013.01); *G16H 15/00* (2018.01); *G16H 50/30* (2018.01)

(56) References Cited

U.S. PATENT DOCUMENTS

| | | | | |
|---|---|---|---|---|
| 2004/0220829 A1* | 11/2004 | Baharav | .................... | G05F 1/14 |
| | | | | 705/2 |
| 2005/0278409 A1* | 12/2005 | Kutzik | .................... | G16H 20/13 |
| | | | | 709/200 |
| 2007/0260492 A1* | 11/2007 | Feied | .................... | G16H 10/60 |
| | | | | 705/3 |
| 2009/0006419 A1 | 1/2009 | Savitsky et al. | | |
| 2010/0312581 A1 | 12/2010 | Wachtell et al. | | |
| 2011/0295773 A1 | 12/2011 | Fisher et al. | | |
| 2013/0018668 A1* | 1/2013 | Goldberg | ............... | G06Q 40/08 |
| | | | | 705/2 |
| 2013/0018670 A1 | 1/2013 | Pankratz et al. | | |
| 2013/0191157 A1 | 7/2013 | Eiden et al. | | |
| 2013/0191159 A1 | 7/2013 | Camacho et al. | | |
| 2014/0058763 A1 | 2/2014 | Zizzamia et al. | | |
| 2014/0100866 A1 | 4/2014 | Wilkerson et al. | | |
| 2014/0200914 A1* | 7/2014 | Rut | ........................ | G16H 70/40 |
| | | | | 705/2 |
| 2014/0244292 A1* | 8/2014 | Rosenberg | ............ | G06F 19/324 |
| | | | | 705/2 |
| 2015/0193583 A1 | 7/2015 | Mcnair et al. | | |
| 2015/0227691 A1 | 8/2015 | Bhattacharya et al. | | |
| 2016/0196407 A1 | 7/2016 | Caballero et al. | | |

OTHER PUBLICATIONS

Non-Final Office Action dated Jan. 10, 2018 for U.S. Appl. No. 14/638,227 of Chanthasiriphan, K. et al., filed Mar. 4, 2015.
Restriction Requirement dated Oct. 18, 2017 for U.S. Appl. No. 14/638,227 of Chanthasiriphan, K. et al., filed Mar. 4, 2015.
International Search Report and Written Opinion dated Apr. 14, 2016, for International Patent Application No. PCT/US2016/012548 filed Jan. 7, 2016, 10 pages.
International Search Report and Written Opinion dated Mar. 29, 2016, for International Patent Application No. PCT/US2016/012551 filed Jan. 7, 2016, 10 pages.
U.S. Appl. No. 14/638,227 by Chanthasiriphan, K. et al., filed Mar. 4, 2015.
U.S. Appl. No. 14/990,766 by Caballero, J. et al., filed Jan. 7, 2016.

* cited by examiner

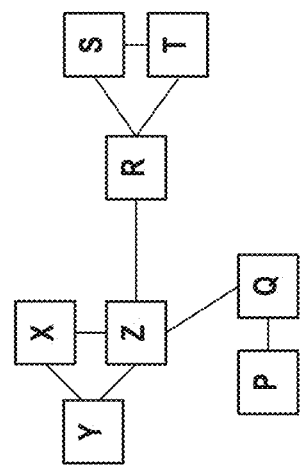
FIG. 8A
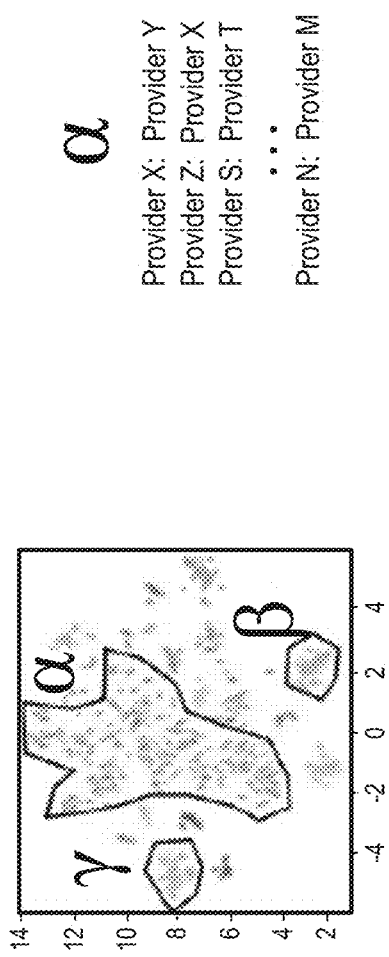
FIG. 8B
FIG. 8C
FIG. 8D
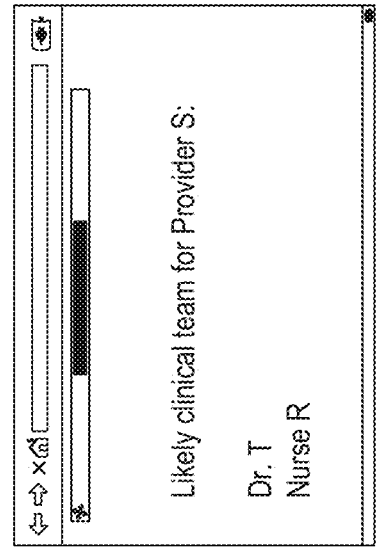
FIG. 8E

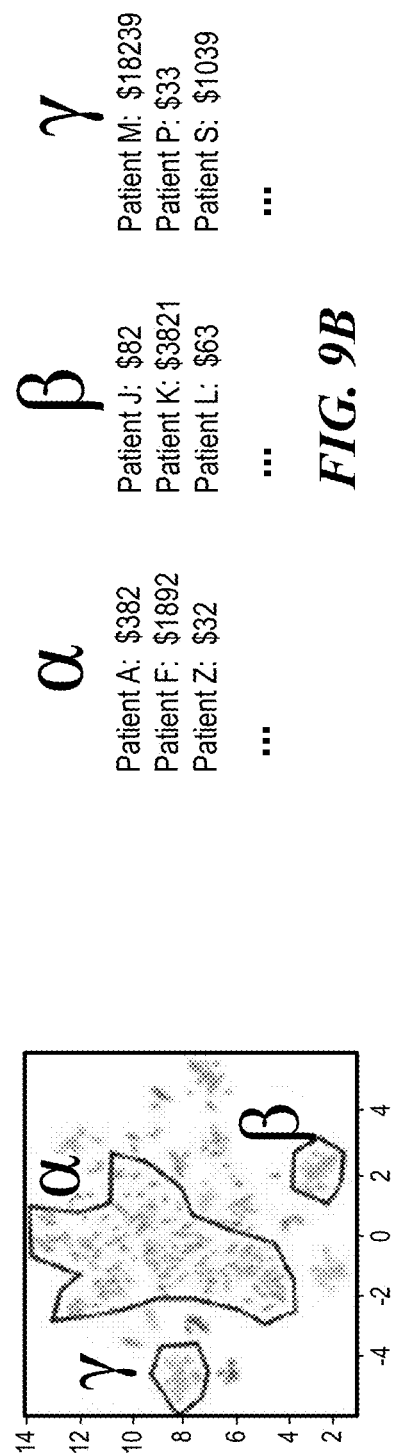
FIG. 9A
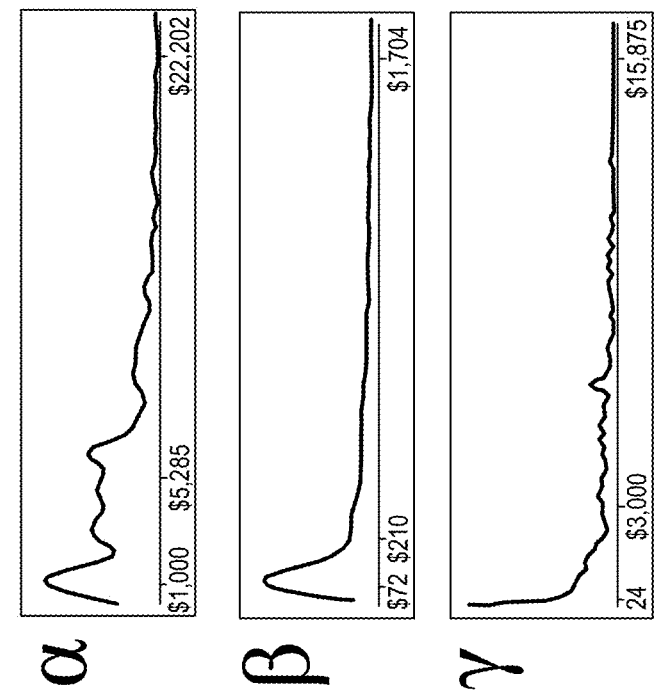
FIG. 9B
FIG. 9C

Cost breakdown

Based on 104,000+ knee replacement surgeries performed in 2012-2014.

HEADS UP

*This cost breakdown currently includes bills from people involved in your care, like your surgeon, anesthesiologist, and physical therapists.*

*We'll be adding hospital bills, health plan coverage and prescription prices soon.*

+ Post-op and rehab    $1,200 - 2,400

✓ HELPFUL    ✗ NOT HELPFUL

REFERENCES

1. Richmond JC. Surgery for osteoarthritis of the knee. The Medical clinics of North America. 2009 Jan;93(1):213-22, xii.

RELATED TOPICS

Hip replacement

Shoulder replacement

Rotator cuff repair

ACL repair

HOME    ABOUT AMINO    JOBS

© AMINO INC.    PRIVACY    TERMS

DATA ANALYSIS MECHANISM FOR GENERATING STATISTICS, REPORTS AND MEASUREMENTS FOR HEALTHCARE DECISIONS

CROSS-REFERENCE TO RELATED APPLICATIONS

This application claims the benefit of U.S. Provisional Patent Application No. 62/100,890, filed on Jan. 7, 2015, the content of which is incorporated by reference herein in its entirety.

FIELD OF INVENTION

Various embodiments relate generally to a data analysis mechanism. More specifically, various embodiments relate to a data analysis mechanism designed for cohort discovery and profiling of healthcare entities.

BACKGROUND

Service providers and device manufacturers are continually challenged to provide a data analysis mechanism designed to generate personalized cost, treatment and outcome predictions by analyzing the insurance claim data of patient populations. Such a data analysis mechanism could help patients make more personalized and effective healthcare decisions.

BRIEF DESCRIPTION OF THE DRAWINGS

These and other objects, features and characteristics of the present embodiments will become more apparent to those skilled in the art from a study of the following detailed description in conjunction with the appended claims and drawings, all of which form a part of this specification. The embodiments of the invention are illustrated by way of example, and not by way of limitation, in the figures of the accompanying drawings:

FIGS. 8A-8E illustrate an example of the proceeding to find affiliated providers from identification of similar providers, according to one embodiment;

FIGS. 9A-9C illustrate an example of the direct calculation of likely cost based on patient clusters and discrete decision groups, according to one embodiment;

DETAILED DESCRIPTION

Figure 1:
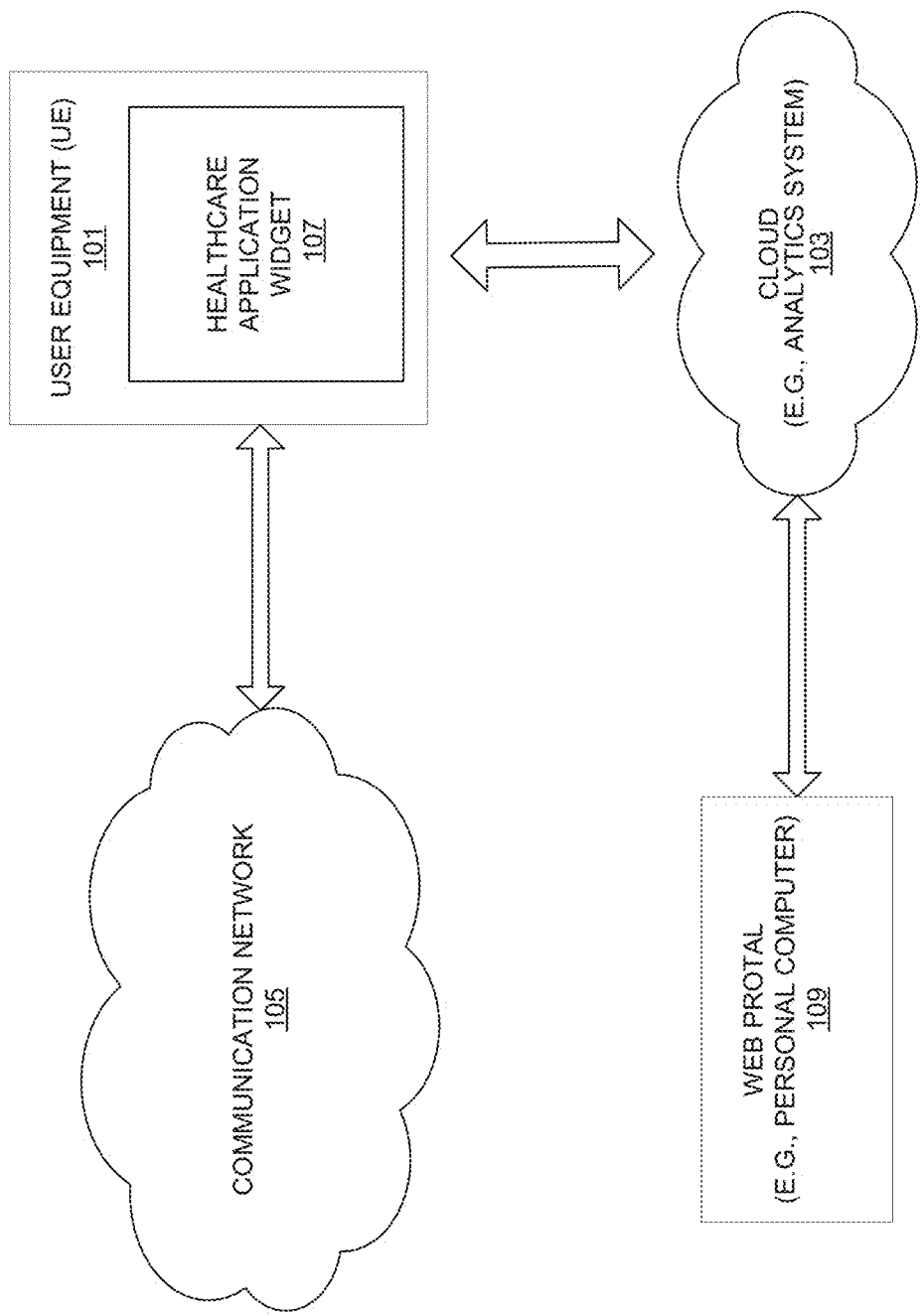
FIG. 1 is a diagram of a system capable of generating descriptive statistics, narrative reports, and quality measurements about healthcare providers and payers by analyzing the insurance claims data of patient populations.

This application is related to providing a data analysis mechanism designed to generate personalized cost, treatment and outcome predictions by analyzing the insurance claim data of patient populations.

According to one embodiment, a method comprises a data analysis mechanism for generating personalized cost, treatment and outcome predictions by analyzing the insurance claim data of patient populations.

The system disclosed in the present application analyzes a large quantity of data to improve medical treatment decisions automatically and efficiently. The system is capable of handling data covering billions of patient-provider interactions, which could take at least tens of years of manpower to process manually. Once primed, the system can then simultaneously handle millions of user queries regarding similar patients and the associated operations and return results within seconds. With a conventional approach, it could easily take weeks to months to yield a response to one of those queries. The historical data typically describes procedures performed on patients in a variety of details. In some embodiments, the system first selects an initial set of patients from the historical data using a set of healthcare criteria, which can correspond to common medical conditions (e.g., prostate cancer), specific patient conditions (e.g., age, gender), etc. Such selection and focus on specific patients saves unnecessary use of computing resources and enables a custom, accurate analysis. The system further distinguishes the initial set of patients in certain ways. For example, the system can distinguish the initial set of patients based on the procedures performed on these patients in several steps. First, the system reduces the set of procedures performed on the initial set of patients by removing those procedures that are not frequently performed or co-performed, that do not have sufficient "importance" ratings as assigned by patients or healthcare professionals, etc. Next, the system clusters the patients with respect to the reduced set of procedures, based on the number of times the procedures in the reduced set are performed, etc. By focusing on only the main clusters, such differentiation of patients makes downstream analysis more efficient and the result more representative. On the other hand, by making several clusters available, such differentiation of patients offers varying analysis to cover varying conditions among patients that satisfy the set of healthcare criteria, thereby achieving flexibility and additional accuracy of analysis.

The downstream analysis involves studying the activities of a specific group of patients, such as those in the largest cluster. Since the specific group of patients is representative of those that satisfy the given set of healthcare criteria, the insight that can be gleaned from the activities of these patients can be helpful to future patients that also satisfy the given set of healthcare criteria. Certainly, the set of procedures performed on the specific group of patients can represent typical treatment plans. Information regarding the healthcare professionals or facilities associated with these procedures can be used to provide referrals to those patients in need. Additional information regarding these procedures can also be used to help those patients properly plan for necessary treatments in terms of time, cost, risk factor, etc. Therefore, through a big-data approach with multiple steps that each aim to minimize the usage of computing resources and maximize the accuracy of analysis results, the system quickly zeros in on relevant information and extracts significant medical insight that is unavailable with existing approaches of looking at isolated data points. Specifically, the system performs efficient information discovery, enabling healthcare professionals and patients alike to intelligently learn from the past experience of an appropriate group of patients and make informed medical decisions.

According to another embodiment, an apparatus comprises at least one processor and at least one memory including computer program code for one or more computer programs; the at least one memory and the computer program code are configured to, with at least one processor, cause, at least in part, the apparatus to provide a data analysis mechanism designed to generate personalized cost, treatment and outcome predictions by analyzing the insurance claim data of patient populations.

According to another embodiment, a computer-readable storage medium includes one or more sequences of one or more instructions that, when executed by one or more processors, cause, at least in part, an apparatus to provide a data analysis mechanism designed to generate personalized cost, treatment and outcome predictions by analyzing the insurance claim data of patient populations.

In addition, for various embodiments, the following is applicable: a method facilitating the processing of (1) data and/or (2) information and/or (3) at least one signal, and the (1) data and/or (2) information and/or (3) at least one signal is based, at least in part, on (or derived at least in part from) any one or any combination of methods (or processes) disclosed in this application as relevant to any embodiment.

For various example embodiments, the following is also applicable: a method is provided for configuring at least one interface to allow access to at least one service, the at least one service being configured to perform any one or any combination of network or service provider methods (or processes) disclosed in this application.

For various example embodiments, the following is also applicable: a method for creating and/or modifying (1) at least one device user interface element and/or (2) at least one device user interface functionality, these devices being based, at least in part, on data and/or information resulting from one or any combination of methods or processes disclosed in this application as relevant to any embodiment of the invention, and/or at least one signal resulting from one or any combination of methods (or processes) disclosed in this application as relevant to any embodiment of the invention.

In various example embodiments, the methods (or processes) can be accomplished on the service provider side or on the mobile device side or in any shared way between the service provider and the mobile device with actions being performed on both sides. The mobile device includes wearable devices such as Fitbit, Smartwatch, Google Glass and so on.

Still other aspects, features, and advantages of the invention are readily apparent from the following detailed description when illustrated by a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

Examples of a method, apparatus, and computer program for a data analysis mechanism to generate personalized cost, treatment and outcome predictions are disclosed below. In the following description, for the purposes of explanation, numerous specific details are set forth in order to provide a thorough understanding of the embodiments of the invention. It will be apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Introduced here are the tools for providing a data analysis mechanism designed to generate personalized cost, treatment and outcome predictions ("the technology"). The tools for helping patients to make healthcare decisions (hereinafter referred to as the "healthcare application") can be implemented in a number of configurations, e.g., as an online application that can be accessed via a communication network such as the Internet, or an application that can be downloaded to and executed on user devices. The user devices can include devices such as a cell phone, smartphone, wireless computer (e.g., laptop, tablet, or PC), personal data assistant (PDA), or other devices. Further, the healthcare application can be accessed on various operating systems, including iOS, Mac, Android, and Windows.

FIG. 1 is a diagram of a system capable of generating descriptive statistics, narrative reports, and quality measurements about healthcare providers and payers by analyzing the insurance claims data of patient populations. Individual patients within the analyzed populations are represented by a de-identified unique patient key (UPK) that allows data on individuals to be joined together longitudinally, without allowing an individual patient's data to be linked to his or her personal identity. The UPKs can be applied to the collection of de-identified health data from diverse sources on a national scale.

UPKs are used to de-identify documents that contain information about transactions, encounters, and/or interactions between individuals and the healthcare system. Primary sources of information include, but are not limited to, insurance claims, electronic health records, personal health records, digitized paper health records, wearable device(s), feedback from individuals collected through online and offline forms and surveys, third-party datasets, accounts receivables and invoices, pharmacy benefits managers, medical, dental, and/or veterinary supply providers, and records of services provided by counselors, social workers, therapists, technologists, and health facility staff.

De-identified UPK data is combined and analyzed to create a holistic picture of an individual's engagement with a national healthcare system over time and to identify cohorts of similar individuals who can be analyzed as a population. The application of UPKs enables the system to analyze massive datasets of secure information and report findings while minimizing the risk of inadvertently disclosing personal health information.

The system uses this method to help individual people select providers and payers for their own care using statistics, reports, and measurements generated from de-identified and linked data in the context of web, desktop and mobile applications. The information presented to people includes the historical and predicted quality and cost of healthcare services for specific medical conditions as well as the historical and predicted quality and cost of services from individual care providers.

Regarding personalized cost, treatment and outcome predictions, historical costs and outcome data for medical conditions, injuries, accidents, illnesses, procedures, surgeries, interventions, treatments, and so forth are computed from health insurance claims data. A user interface is presented for a user to input personal attributes (e.g., age, gender, location, insurance plan, and medical history) and select one or more conditions or procedures. Future costs, treatments, and outcomes are extrapolated by mapping the computed historical data to the user's attributes and adjusting them using additional external data sources (e.g., healthcare inflation index). The future costs, treatments, and outcomes are presented to the user using text, images and charts. According to one embodiment, the mechanism by which this process is conducted may rely on the user entering health-relevant information beforehand, and/or it may rely on the user's IP address and/or device locations services without the user having to enter such information, such that personalized information based on the user's characteristics is generated. In some other embodiments, this includes a personalized presentation of likely procedures and related costs customized to the user, with sufficient information and detail to outline an expected set of events and costs for that person, should the person see a doctor for treatment.

As shown in FIG. 1, the system 100 comprises a smart device (a user equipment or UE) 101 having a healthcare application 107 installed and having connectivity to a web portal (e.g., personal computer) 109 via a cloud network 103. By way of example, the communication network 105 of the system 100 includes one or more networks such as a data network, a wireless network, a telephony network, or any combination thereof. It is contemplated that the data network may be a local area network (LAN), a metropolitan area network (MAN), a wide area network (WAN), a public data network (e.g., the Internet), a short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

The UE 101 is any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistant (PDA), audio/video player, digital camera/camcorder, positioning device, television receiver, radio broadcast receiver, electronic book device, game device, an accessory or peripheral of these devices, or any combination thereof. It is also contemplated that the UE 101 can support any type of interface to the user (such as "wearable" circuitry).

By way of example, the UE 101, the cloud 103 and the web portal 109 communicate with each other and other components of the communication network 105 using well known, new, or still developing protocols. In this context, a protocol includes a set of rules defining how the network nodes within the communication network 105 interact with each other based on information sent over the communication links. The protocols are effective at different layers of operation within each node, from generating and receiving physical signals of various types, to selecting a link for transferring those signals, to formatting information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 2:
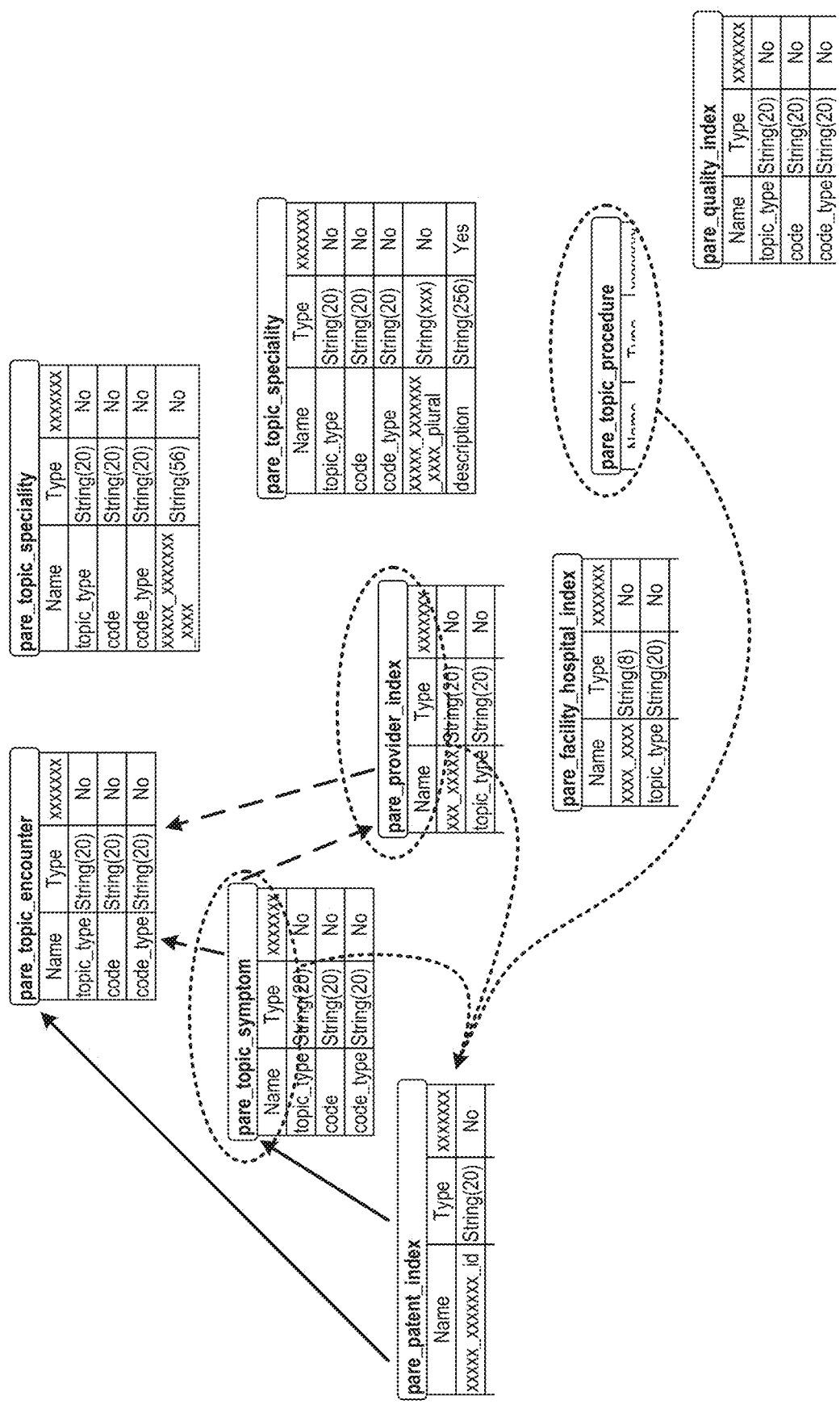
FIG. 2 is a flow diagram of a process for generating consumer-friendly structured vocabularies and mapping, according to one embodiment.
Figure 3:
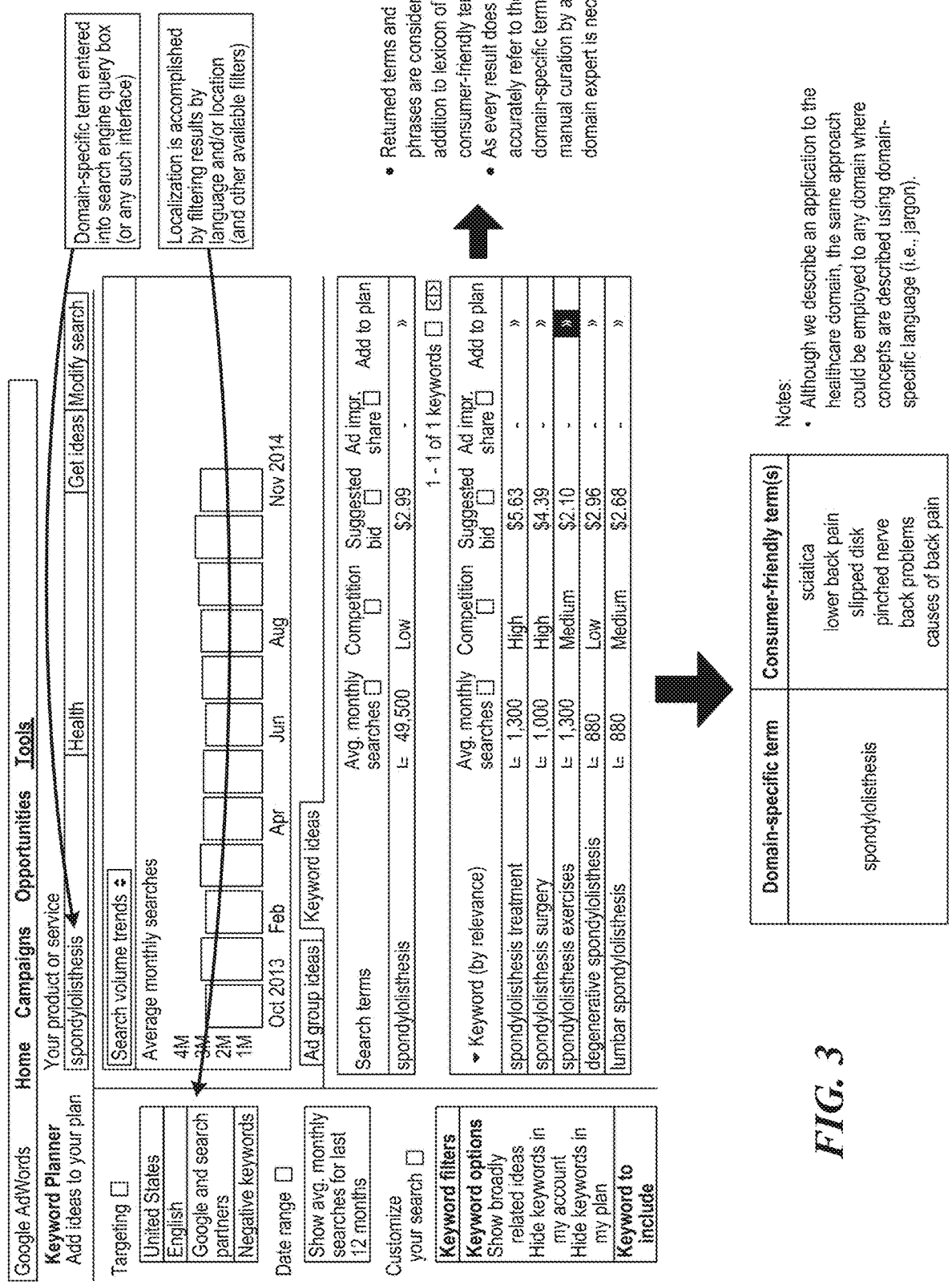
FIG. 3 is a flow diagram of a process for generating consumer-friendly structured vocabularies and mapping, according to one embodiment.
Figure 4:
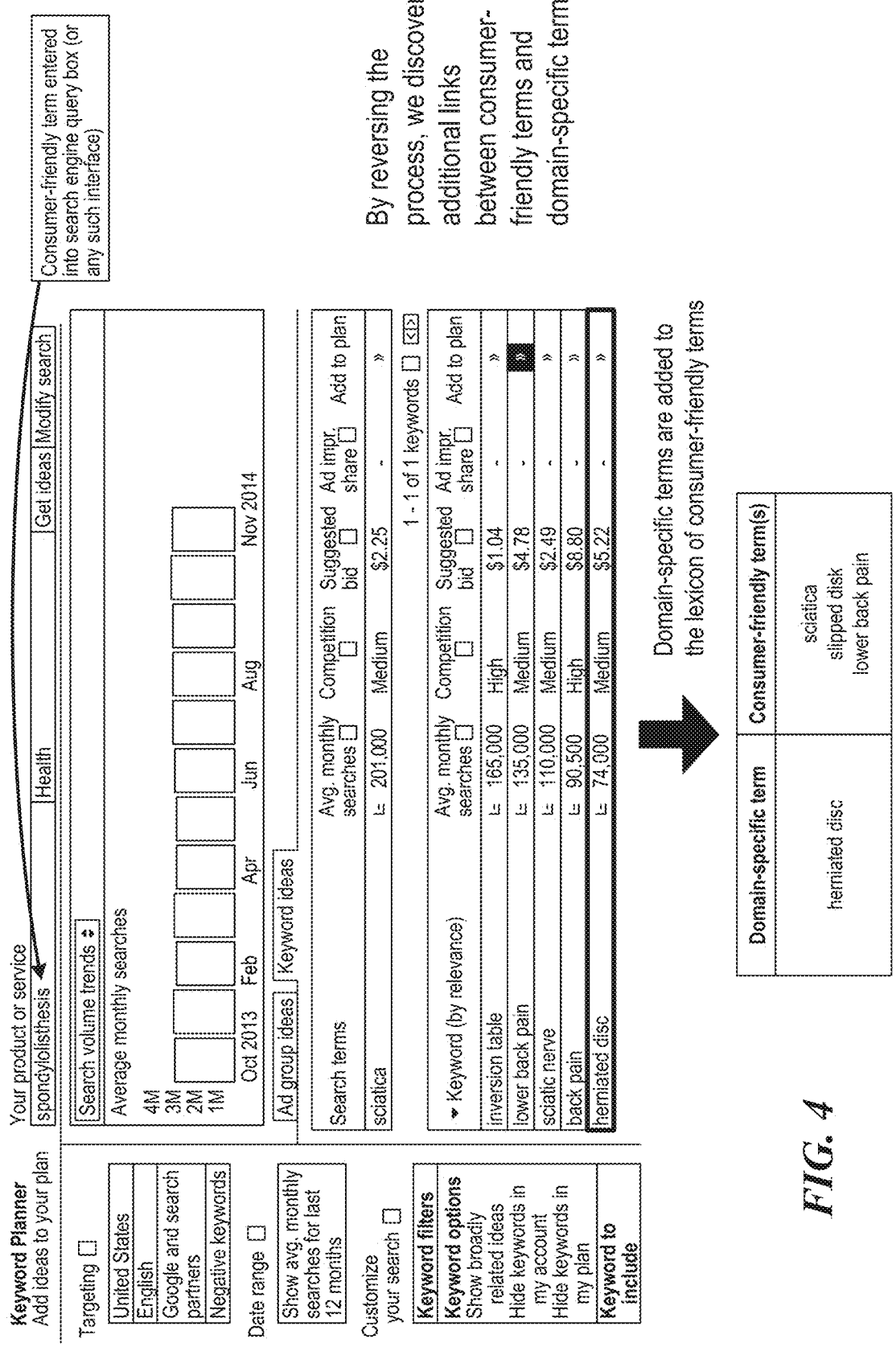
FIG. 4 is a flow diagram of a process for generating consumer-friendly structured vocabularies and mapping, according to one embodiment.
Figure 5:
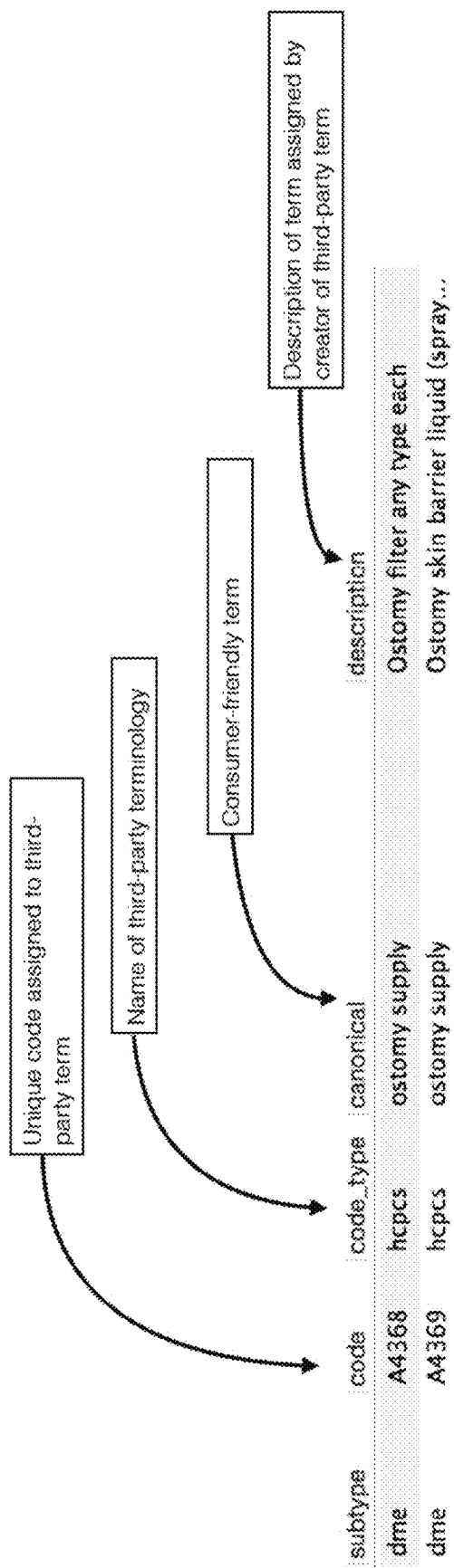
FIG. 5 is a flow diagram of a process for generating consumer-friendly structured vocabularies and mapping, according to one embodiment.
Figure 6A:
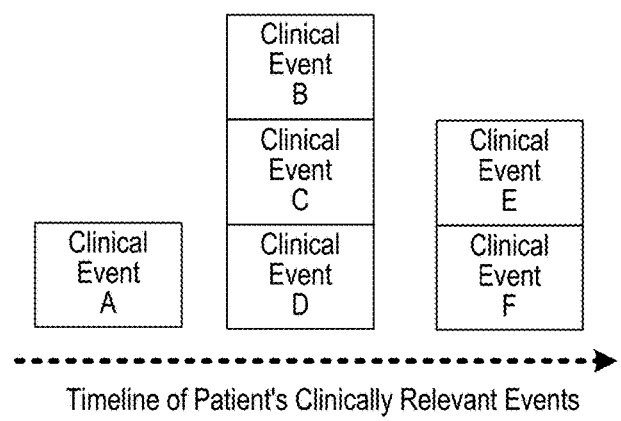
FIGS. 6A-6E illustrate an example of the phases of time-oriented raw medical data for patient cohorts and decision groups, according to one embodiment.
Figure 6C:
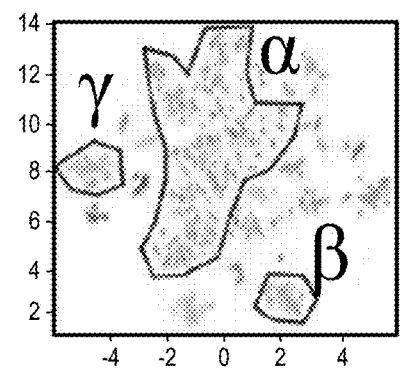
Figure 6B:
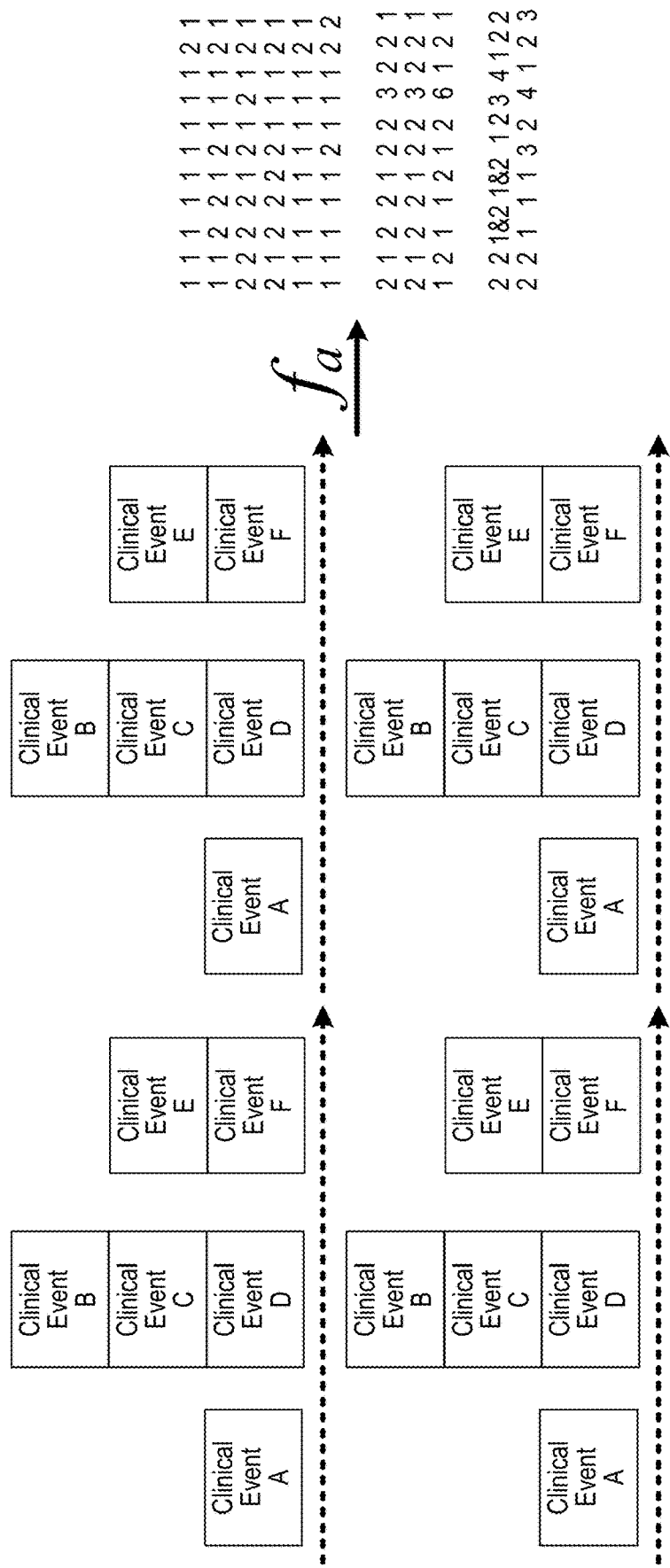
Figure 6D:
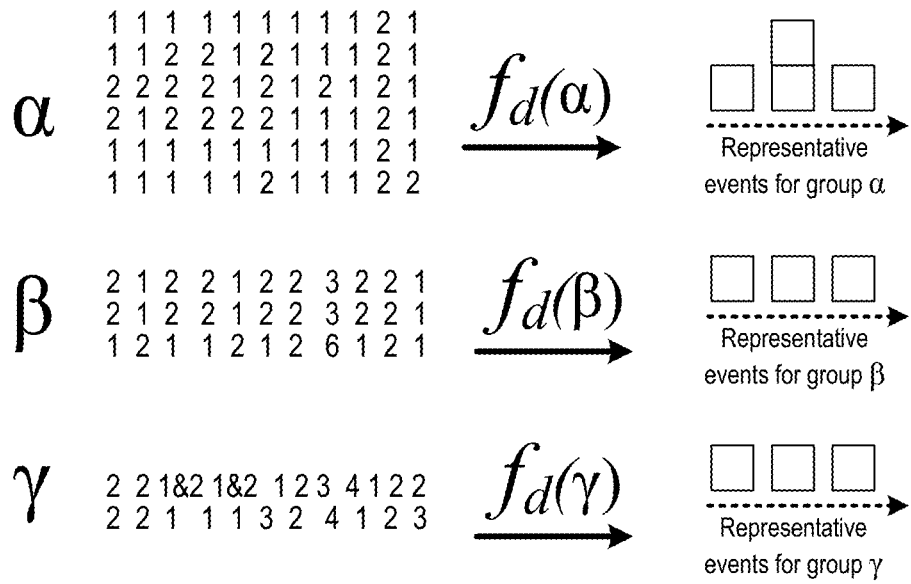
Figure 6E:
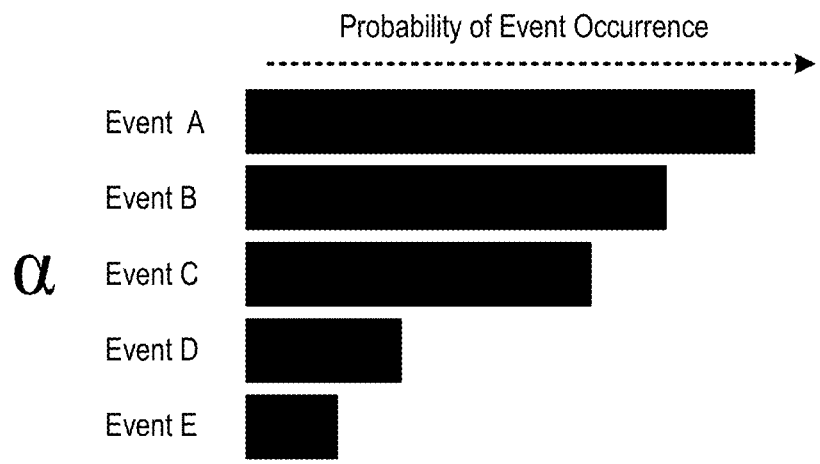

FIGS. 2-4 are flow diagrams of a process for generating consumer-friendly structured vocabularies and mappings, according to one embodiment. Regarding consumer-friendly structured vocabularies and mappings, there is no known comprehensive vocabulary of healthcare terms used by laypeople ("consumer-friendly terms"); there is no known crosswalk between consumer-friendly terms and generally accepted medical terminology. We present a means of (1) generating a comprehensive collection of consumer-friendly terms, (2) mapping consumer-friendly terms to existing third-party medical terminologies, and (3) describing relationships between entities in the healthcare subdomain represented by consumer-friendly terms.

Regarding how to generate a comprehensive collection of consumer-friendly terms, the approach to discovering consumer-friendly terms involves using historical data provided by Internet search engines to generate rank-ordered lists of health-related phrases. This innovative approach allows one to expeditiously create language-specific and region-specific dictionaries of consumer-friendly healthcare terms.

In order to map consumer-friendly terms to existing third-party medical terminologies, consumer-friendly terms are individually mapped to concepts found in third-party lexicons by a healthcare professional. This manually curated process involves a comparison of semantic meaning. The end result of this process is a thesaurus that maps consumer-friendly medical terms to one or more third-party terminologies. This key innovation allows one to query healthcare data from a multitude of sources using consumer-friendly language.

In order to describe relationships between entities in the healthcare subdomain represented by consumer-friendly terms, individual consumer-friendly terms are categorized into one or more of the following: providers (training level, specialty, role in healthcare encounter); facilities (size, specialty, geographic location); conditions (acuity, severity, treatment options); procedures and their attributes (intent, invasiveness, place of service); medications (intent, route, dose, indication); form of medication (oral, liquid, capsule, etc.); equipment (function, vendor, cost); devices/implants (function, vendor, cost); services (intent, cost); payers (name, relationship to consumer); and patient attributes (medical history, surgical history, family history, habits, etc.).

Semantic descriptors are used to define the relationships across and within categories. Potential relationships between categories are discovered through statistical inference and/or clinical experience.

Regarding Semantic Relationships:

(1) A minimum number of relationships are defined manually, as guided by a human understanding of the healthcare system of interest. As a result, the system has the ability to describe known interactions within and between healthcare subdomains using consumer-friendly terms.

(2) An infinite number of derivative semantic relationships are computed using advanced statistical methods and machine learning algorithms. As a result, the system has the ability to discover novel interactions within and between healthcare subdomains using consumer-friendly terms.

(3) Our approach to describing and defining healthcare subdomains allows us to discover novel categories within healthcare subdomains. These categories are combinatorial sets of instances from two or more distinct categories.

Examples of Semantic Relationships:

(1) Manually defined relationship [solid line in FIG. 2]: (a) The health of at least one patient is the topic of discussion during a health-related encounter. (b) A patient experiences a symptom.

(2) Derivative relationship [dashed line in FIG. 2]: (a) A patient experiences hemorrhage, a symptom, which forms the rational basis for an encounter of acute medical care. (b) The life-threatening nature of the symptom influences the selection of providers involved in the patient's care to include emergency medicine physicians.

(3) Novel category and its relationships [dotted lines in FIG. 2]: (a) Because the skill set of emergency medicine physicians is a subset of all health-related procedures, the system can infer the definition of a novel category called "procedures performed by emergency medicine physicians for the treatment of hemorrhage." In this example, the novel category is formed by combining instances from the procedure, provider, and symptom categories. (b) Having described our novel category, the system can now define its relationship to the patient (or any other category).

Regarding data analysis methods, the data analysis methods described below are applied to data generated when people interact with healthcare providers and payers. Data analysis methods and related extensions are used to identify, segment, and describe "patient cohorts" and patient decision groups, which are populations of people with similar characteristics. Patient cohorts may share any combination of characteristics, including (but not limited to) sex, age, location, medical diagnoses, medical history, medical system utilization, insurance plan, and insurance plan utilization. Further, data analysis methods of patient cohorts comprise the following: (A) Data analysis methods to determine an expected set of events for a given patient and the patient's related cohort. Expected events are determined by their frequency of co-occurrence with other events, not simply by rank order of occurrence frequency. (B) Data analysis methods for the automatic determination of sets of procedure groups, which constitute individual decision groups, where one group is one plausible alternative for a given patient's treatment. These methods permit a patient to view the expected events he or she is likely to undergo, as well as other groups of events that present possible, though less probable, alternatives, controlling for overall frequency.

The steps taken to determine both an expected set of events and procedure decision groups are illustrated in FIGS. 6A-6E, and involve the following: Given specific patient characteristics, such as age, gender, geographic location, conditions and comorbidities, and imputed values (such as patient risk for diabetes), sufficient medical data is gathered within some timeframe where each medical event can be discretely identified and assigned some relative date of occurrence. These characteristics are chosen by the user and are an important first step because they focus all subsequent results on a very identifiable, and user-customizable, demographic relevant to the user.

For each patient, these events can be represented quantitatively by reducing them to a numeric matrix where each row i is a patient and each column j is an event, as illustrated in step (B) of FIGS. 6A-6E below. The values in each cell (i,j) are a numeric representation of that patient's experience with that event, e.g., the number of times the patient had that event occur within some set timeframe or a weighted level of importance of that event for that patient. Importantly, this value's importance is relative only to other patients and other events, and thus many functions can satisfy the generation of the value in (i,j).

Because the resulting matrix is assuredly of very high dimensionality, its complexity is reduced using a second mathematical transformation. This transformation serves to limit the number of columns (events) in the matrix, while retaining the same number of rows (patients). Examples of functions that satisfy this transformation include using only a certain number of the most common events, weighting events by rarity (e.g., via term frequency-inverse document frequency), and taking some high-ranking column subset, or by projection methods that identify and map data to two or more orthogonal planes (such as principal component analysis). Regardless of the reduction technique ($f\_b$), the result is a new data matrix composed of fewer columns that still meaningfully describe each individual patient's medical experience relative to others, albeit in reduced form.

Once a reduced feature matrix is generated, clustering techniques ($f\_c$) are employed to identify groups of patients (and events) that are similar. Each point in the clustering procedure is an individual patient, described by their reduced event form. Importantly, the effectiveness of clustering at this stage is improved due to the reduction conducted in the prior step, and the final output of the clustering step is a distinct grouping of patients that are similar to each other in medical events. Moreover, it is at this point that distinct individual decision groups are manifest. For example, the largest cluster is likely the most common set of events for that patient demographic, and the second-largest may be an alternate set of medical events driven by an important comorbidity. In this way, multiple patient types and medical courses of action are identified quantitatively.

For each identified cluster, a scoring function is used to rank patient experiences by how representative they are of the cluster to which they belong, with a final output in this stage a set of discrete medical events. A simple example of a function here is selecting the set of events in each cluster above some probability cutoff (maximum likelihood). Ideally, however, this scoring function would take advantage of the correlations between events, as well as the probability of each event occurring, to identify a representative set of events for the cluster. Thus, a scoring function, $f\_d$, is run for each patient (row) in the non-reduced event matrix.

Finally, the set of medical events selected after the scoring phase, as well as the events' original likelihood, is presented to the user as an informative illustration. Note that this final result is a representation to the user of a common set of medical events for patients with certain characteristics and can be generated for arbitrary timeframes (e.g., a one-year span for young males with asthma, or 30 days after a medical procedure for all females in Dallas, Tex.). Importantly, because the occurrence of each event is used for the functions, and not the precise time, the approach will work in cases where event timing is poorly understood, or even absent, as long as the event is known to have occurred within some rough timeframe.

FIGS. 6A-6E illustrate an example of the phases time-oriented raw medical data undergoes for cohort selection of a representative encounter, according to one embodiment. There are five core steps: (A) for each patient of interest with specific cohort characteristics, such as age, gender or geographic location, medical record data exists that can be sorted according to some date (such as the date of an event or the charge date in a claim); (B) the records are transformed using a function, such as log of the number of events per patient, $f\_a$, into a numeric matrix such that each row corresponds to an individual patient and each column to a type of clinically relevant event; (C) the dimensionality of the numeric matrix is reduced via $f\_b$ (for example, using projection methods) and grouped using $f\_c$ (using hierarchical clustering techniques) such that patients who experience similar events are placed in the same cluster (in the above plate, alpha, beta and gamma, delineated by solid lines, represent three possible clusters; (D) for each identified cluster, a scoring function $f\_d$ is used to identify the most quantitatively representative patient encounter; and (E) for each cluster, the empirical probability of the events in the representative patient encounter is displayed to the user.

Data analysis methods are used to identify, segment, and describe "provider cohorts," which are populations of providers with similar characteristics. Provider cohorts may share any combinations of characteristics, including (but not limited to) sex, age, location, medical specialties and subspecialties, medical facility affiliations, medical school(s) attended, medical board certifications, patient cohorts treated, medical services rendered to patients, and insurance plans accepted.

The methods used for describing and segmenting patient cohorts can be employed to determine practice-based provider cohorts, with some minor adjustments. Whereas for patient cohorts initial filtering is done based on demographic information, presently the system can filter patients based on provider type. For example, only patients of and patient events done by gastroenterologists would constitute a provider-based characteristic. The process noted for patient cohorts would then proceed as before, and an additional step would take place at the conclusion of phase (C). Throughout the steps outlined for patient cohort selection, the provider is also tracked per patient. When clustering at phase (C) is conducted, the providers in each group (e.g., groups alpha, beta, and gamma) can be identified as being similar. The precise determination of similarity can be done purely on the co-occurrence of the providers in a group, or thresholds (by count, e.g., minimum number of patients per provider, or by fraction, e.g., a certain percentage of patients in a group for each provider) may be used to present a truncated list.

Figure 7:
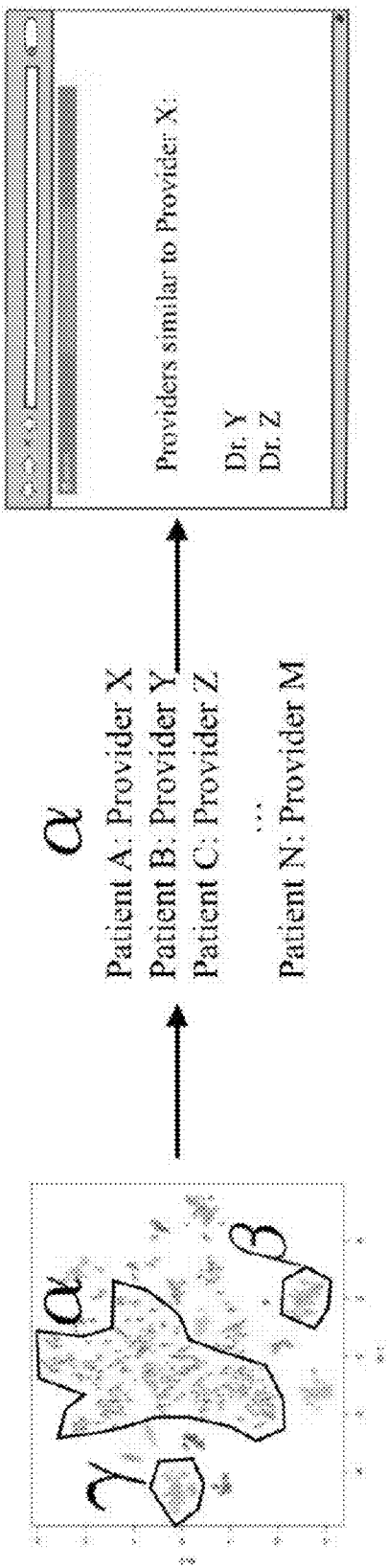
FIG. 7 illustrates an example of the extension of the patient cohort and decision group identification process for providers, according to one embodiment.
Figure 10A:
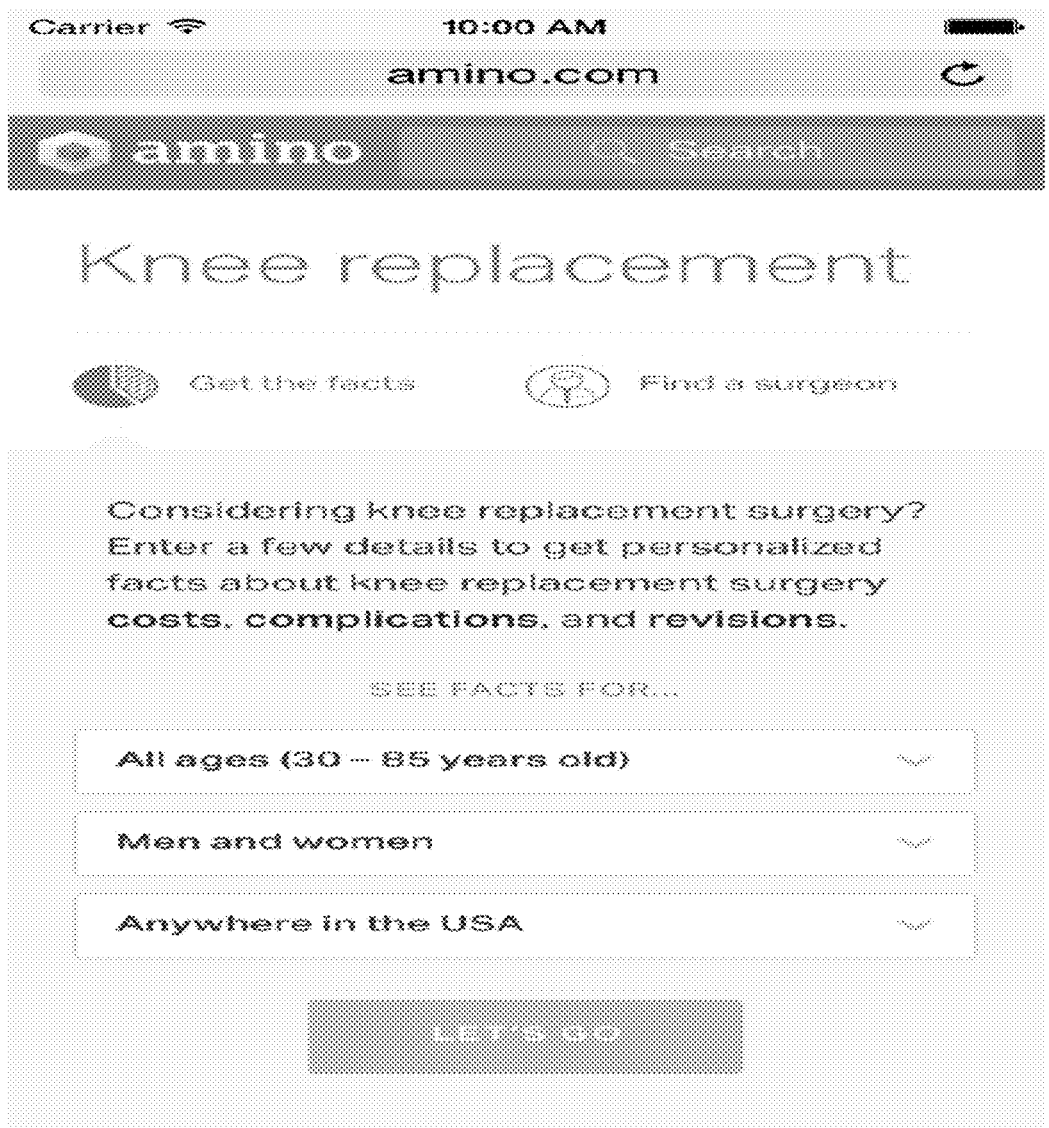
FIGS. 10A-10F illustrate an example of a graphical user interface of the healthcare application of FIG. 1 for providing personalized cost, treatment and outcome predictions, according to one embodiment.
Figure 10B:
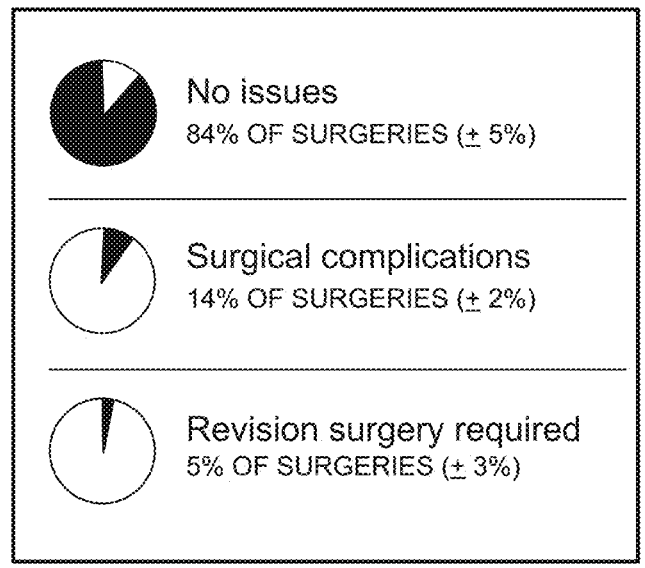
Figure 10C:
Figure 10D:
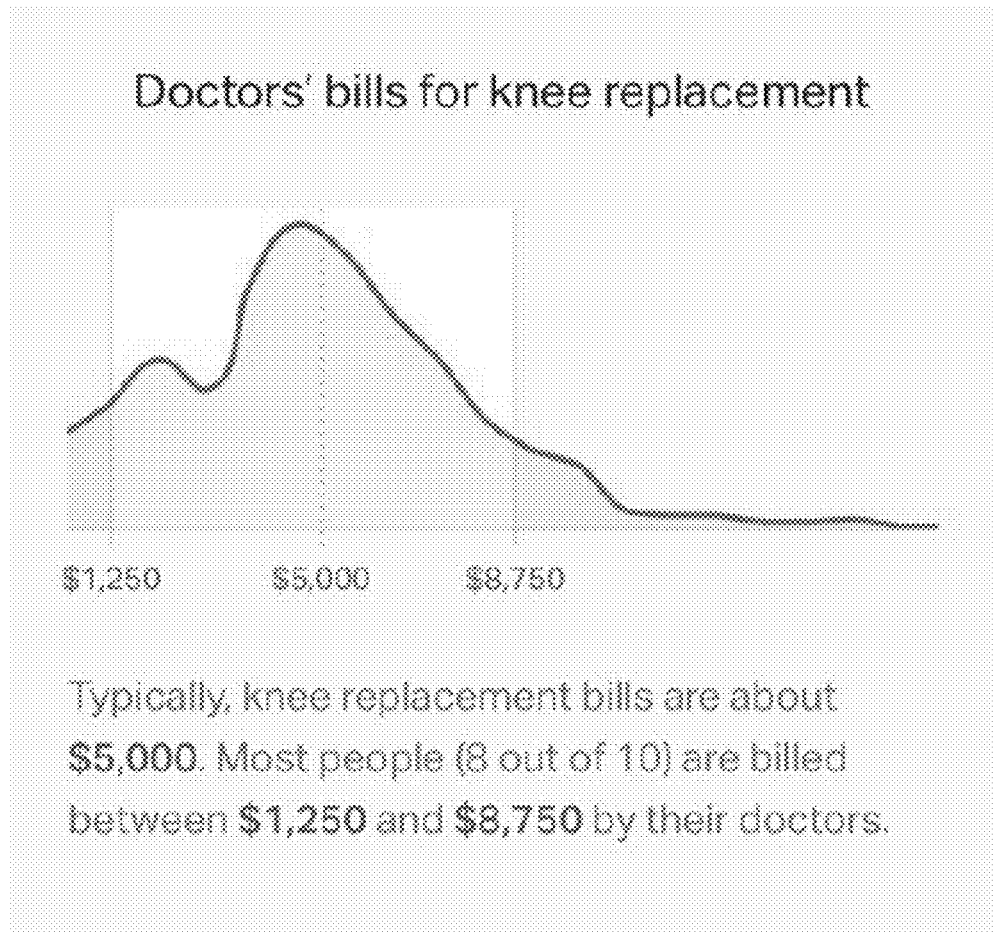
Figure 10E:
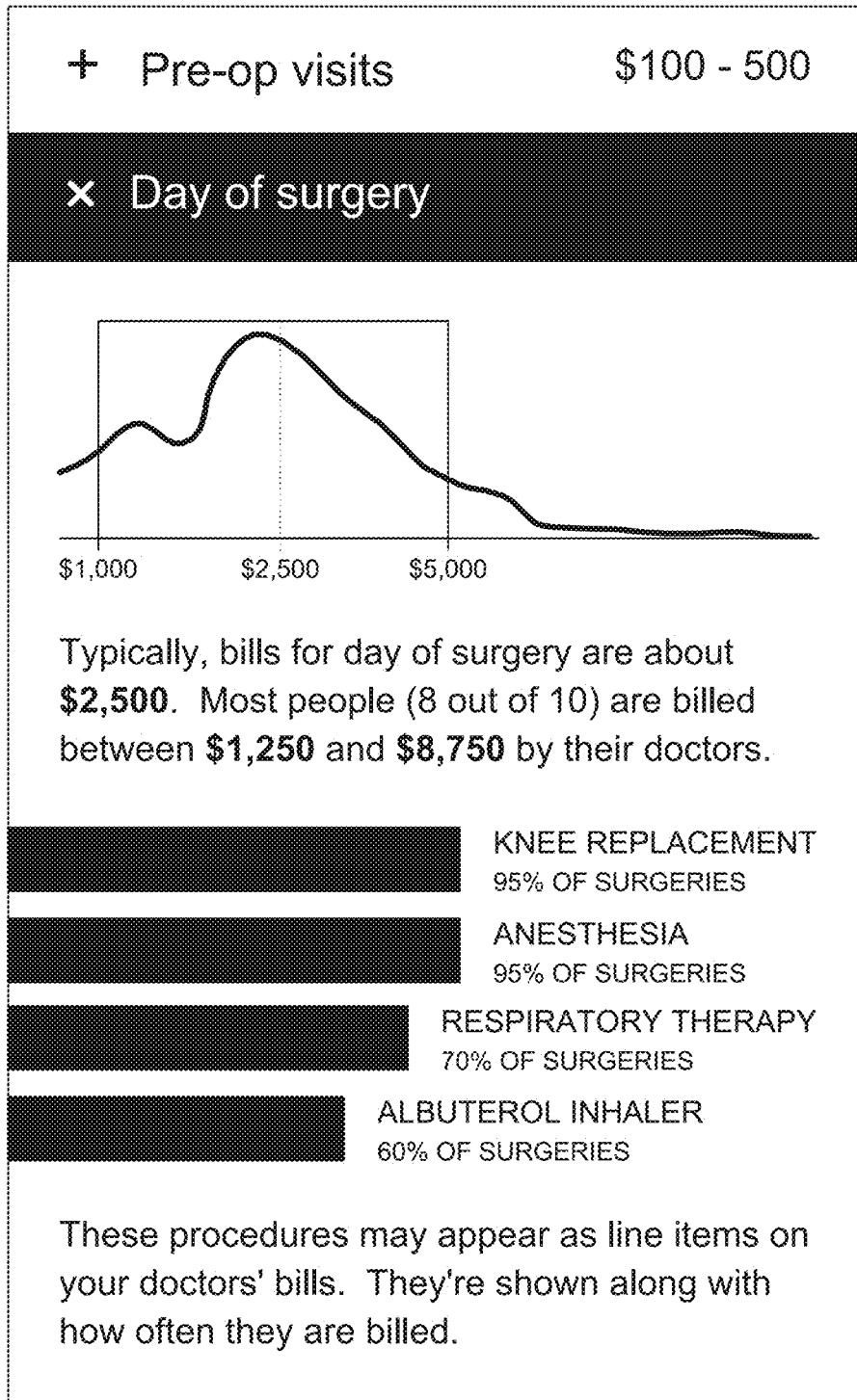
Figure 10F:
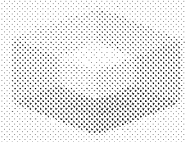

FIG. 7 illustrates an example of the extension of the patient cohort and decision group identification process for providers, according to one embodiment. Continuing at phase (C), the providers for patients in each distinct group (in the above example, group alpha) are identified and presented to the user as similar to each other for the purposes of finding relevant providers.

While the above takes into account identifying and presenting to the user sets of providers by similarity, additional views are generated based on affiliation; that is, sets of providers are generated that may not necessarily be related as defined in [0065] but perhaps belong to a similar referral network or are otherwise found to be cooperating with each other over the same patients (cf. FIGS. 8A-8E).

Based on the user's specific personalization of the characteristics of interest (age, gender, geographic location, etc.), the system constructs a clustering, per-patient cohort methodology (A). Likewise, per identifying similar providers, a mapping is generated (B); however, for the purposes of affiliated providers, unlike similar providers, this mapping is based on provider relation. Here, the system defines relation as any relationship that connects two providers together, such as patient referral, practice facility, or even shared patients. This is computed directly from the medical data, and relates in 1:1 form a provider with other providers. In 1:1 form, these relations are translated into an adjacency matrix thusly: define C as the set of providers that treated a group of patients in a cluster, and let $p\_x$ represent any provider within C. Suppose $R(p\_p\_j) > 0$ if a relation exists between providers $p\_i$ and $p\_j$, and $R(p\_p\_j) = 0$ otherwise; then define a matrix M, where each value $M\_\{i,j\} = R(p\_p\_j)$, such that M is directly interpretable as an adjacency matrix. M is then used to construct a network of provider relationships (C), upon which modularity/community detection algorithms are employed to identify groupings of providers (D). These groups can then be presented to the user as sets of providers, specific for the characteristics they defined prior, that are strongly related to any other provider. Notably, this can be done on a user-specified basis on a subset of providers, and thus is personalized to the individual user.

FIGS. 8A-8E illustrate an example of the process to find affiliated providers from identification of similar providers, according to one embodiment. Starting again at the clustering phase (A), the system generates a list of similar providers based on clustering. Connections are constructed such that each provider may connect to one or more other providers based on referral, shared patients or other useful characteristics (B). This amounts mathematically to an adjacency matrix, from which a network is constructed (C) (note that the edges in this network may be weighted by additional information, such as frequency of referral or number of patients). Any number of known community detection techniques are then used to identify groups of providers that relate to each other (D). Finally, an interface is presented to the user that lists a likely care/provider team for that user's set characteristics. In the above example, a related group of providers R, S and T is identified and presented to the user.

Data analysis methods are used to identify, segment, and describe characteristics of "facility cohorts," which are collections of facilities with similar characteristics. Facility cohorts may share any combination of characteristics, including (but not limited to) location, facility type, affiliated facilities, affiliated physicians, affiliated physician cohorts, facility size attributes, facility departments, facility accreditation, patient cohorts treated, medical services rendered to patients, and insurance plans accepted. As for providers, extensions to the patient cohort approach can track facilities during phase (C), resulting in facilities that share similar treatment regimes. In practice, the matrix and thus the network generated to extend the provider cohort approach (cf. FIG. 8) to facilities requires additional relationships between facilities, such as providers affiliated with more than one facility and geographic distance.

Regarding data analysis methods used to predict medical event costs over time, during the calculation of medical event groupings and representative medical events for a set of patients with a given characteristic, the system can simultaneously generate a prediction of the overall cost. While tracking patient costs throughout the process, the system adds another extension at the clustering step. If medical cost data is provided at the event level, the system aggregates up to the patient level for a specified timeframe; otherwise, if costs are at the patient level, they are retained. Total aggregate costs for each patient are calculated for each grouping, and using density estimation techniques, a cost curve is imputed for presentation to the user. This provides the user with a personalized estimate of costs by patient cohort/decision group type, customized by the patient's predefined age/gender/geographic location/etc. characteristics for any procedure or condition.

FIGS. 9A-9C illustrate an example of the direct calculation of likely cost based on patient clusters and discrete decision groups, according to one embodiment. For each grouping identified in the patient clustering phase (A), per-patient costs are calculated at the service line level and aggregated up to the total patient cost for the given timeframe (B). Density estimation techniques are then used to smooth over the costs and provide to the user an imputed cost curve representing an expected cost span for the patient demographics and characteristics of choice (C). Depending on the timeframe set, this can be done to predict cohort costs for a medical procedure, annual cost for a chronic condition, chemotherapy treatment on a monthly basis, etc.

FIGS. 10A-10F illustrate an example of a graphical user interface of the healthcare application of FIG. 1 for providing personalized cost, treatment and outcome predictions, according to one embodiment.

Regarding visualizations, user interfaces, and application functionality, user interfaces allow users to select any cohort about which to display historical data and/or predictions about what events that cohort may experience with regards to a specific medical condition, medical procedure, medical specialty, geographical region where care is received, medical facility type, specific care provider, specific care facility, medical device, medication, health insurance network, health insurance plan, other medical treatment, or other type of medical encounters.

For any given topic (medical condition, medical procedure, etc.), the user interface provides one or more filters that allow the user to specify one or more attributes of the cohort of interest.

The number of options available in each filter is the smallest number of options required to offer the user the maximum number of statistically meaningful variations in the resulting data, as determined by our data analysis methods.

User interfaces may show historical data and predictions about interactions between patient cohorts, individual providers, provider cohorts, individual facilities, facility cohorts, individual health plans, health plan cohorts, and other concept cohorts. User interface components include (1) the cohort selector described above; (2) a collection of one or more episodes of medical care experienced by a given cohort for a specific medical condition, treatment, or other medical encounter of interest; and (3) individual episodes of care represented as expandable and collapsible sections in the user interface, where descriptive labels and summary statistics about the episode appear in the collapsed state.

The user interface for the collapsed state allows a user to click, hover, voice command, or tap to see the expanded state. In the expanded state, the episode is represented more granularly with graphical and textual representations of treatment components, outcomes, types of care providers and facilities involved, billed costs, remitted costs, patient out-of-pocket costs, and other aspects of the medical care involved. In the expanded state, descriptive numerical statistics are incorporated into the graphical and textual components to illustrate concepts including, but not limited to, the observed frequency of an event, the predicted likelihood of an event, averages, ranges, percentiles, standard deviations, and margins of error. In both the expanded and collapsed views, the user interface provides tooltips: visual elements which, when clicked, tapped, voice commanded or hovered, allow users to see more detailed narrative descriptions about the episode of care or its constituent parts.

User interfaces may provide personalized "call to action" links to other relevant portions of the application based on their selected cohort and a given medical topic. Types of calls to action include:

Calls to action to visit historical data and predictions for topics related to the topic the user is currently viewing (e.g. a user viewing information on spinal fusion surgery might, for some cohort selections, see a prompt to visit the related topic of back pain).

Calls to action to search for individual medical care providers related to the topic the user is currently viewing (e.g., a user viewing information about breast cancer treatment for the cohort of females in the New York City area would see a link to find a breast cancer specialist in the New York City area using our application's doctor search functionality).

Figure 11:
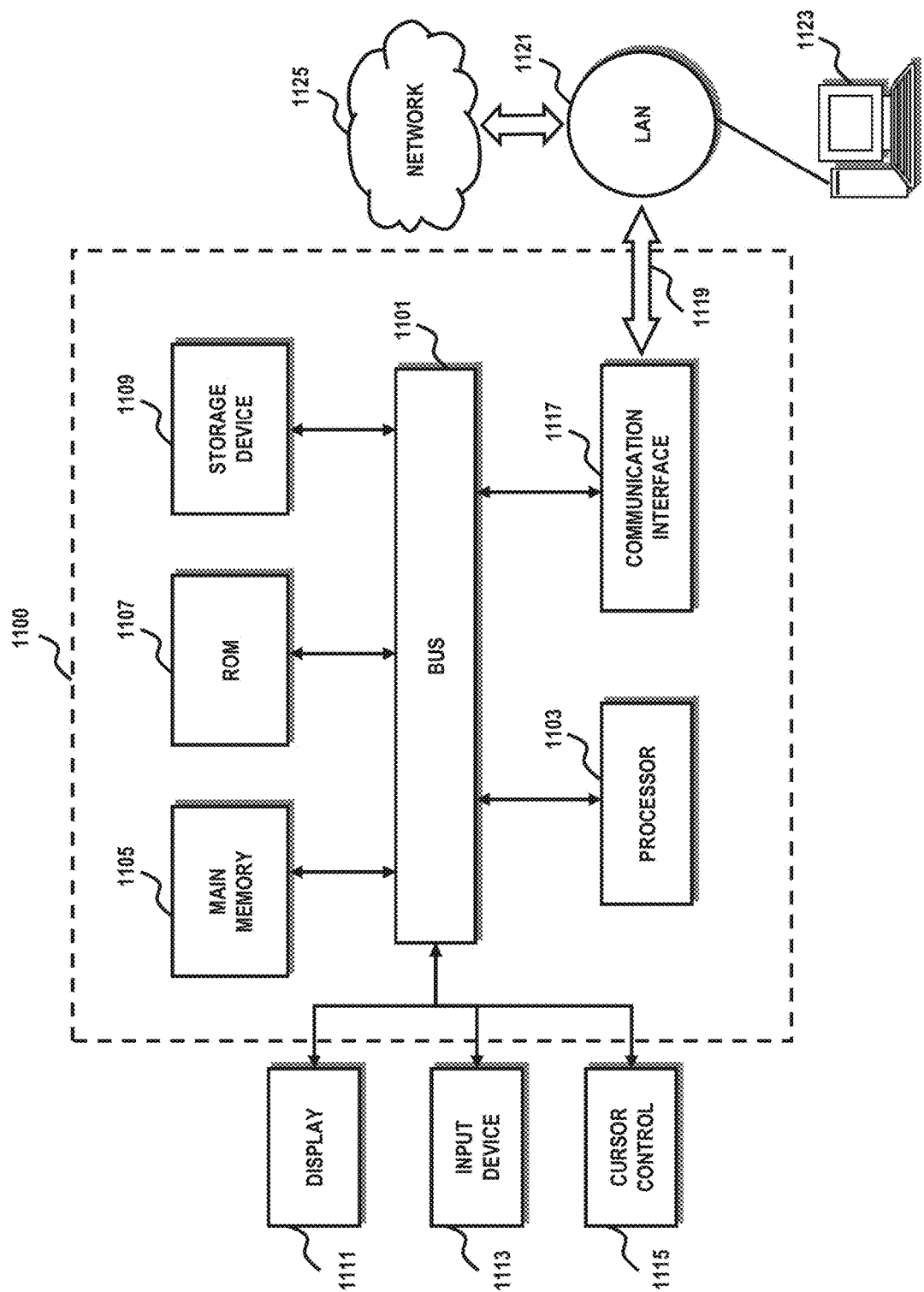
FIG. 11 is a diagram of a computer system that can be used to implement various exemplary embodiments.

FIG. 11 is a diagram of a computer system that can be used to implement various exemplary embodiments. The computer system 1100 includes a bus 1101 or other communication mechanism for communicating information and one or more processors (of which one is shown) 1103 coupled to the bus 1101 for processing information. The computer system 1100 also includes main memory 1105, such as a random access memory (RAM) or other dynamic storage device, coupled to the bus 1101 for storing information and instructions to be executed by the processor 1003. The main memory 1105 can also be used for storing temporary variables or other intermediate information during execution of instructions by the processor 1103. The computer system 1100 may further include a read only memory (ROM) 1107 or other static storage device coupled to the bus 1101 for storing static information and instructions for the processor 1103. A storage device 1109, such as a magnetic disk or optical disk, is coupled to the bus 1101 for persistently storing information and instructions.

The computer system 1100 may be coupled via the bus 1101 to a display 1111, such as a cathode ray tube (CRT), liquid crystal display, active matrix display, or plasma display, for displaying information to a computer user. An input device 1113, such as a keyboard including alphanumeric and other keys, is coupled to the bus 1101 for communicating information and command selections to the processor 1103. Another type of user input device is a cursor control 1115, such as a mouse, a trackball, or cursor direction keys, for communicating direction information and command selections to the processor 1103 and for adjusting cursor movement on the display 1111.

According to an embodiment of the invention, the processes described herein are performed by the computer system 1100, in response to the processor 1103 executing an arrangement of instructions contained in the main memory 1105. Such instructions can be read into the main memory 1105 from another computer-readable medium, such as the storage device 1109. Execution of the arrangement of instructions contained in the main memory 1105 causes the processor 1103 to perform the process steps described herein. One or more processors in a multi-processing arrangement may also be employed to execute the instructions contained in the main memory 1105. In alternative embodiments, hard-wired circuitry may be used in place of or in combination with software instructions to implement the embodiment of the invention. Thus, embodiments of the invention are not limited to any specific combination of hardware circuitry and software.

The computer system 1100 also includes a communication interface 1117 coupled to the bus 1101. The communication interface 1117 provides a two-way data communication coupling to a network link 1119 connected to a local network 1121. For example, the communication interface 1117 may be a digital subscriber line (DSL) card or modem, an integrated services digital network (ISDN) card, a cable modem, a telephone modem, or any other communication interface to provide a data communication connection to a corresponding type of communication line. As another example, communication interface 1117 may be a local area network (LAN) card (e.g., for Ethernet™ or an Asynchronous Transfer Model (ATM) network) to provide a data communication connection to a compatible LAN. Wireless links can also be implemented. In any such implementation, communication interface 1117 sends and receives electrical, electromagnetic, or optical signals that carry digital data streams representing various types of information. Further, the communication interface 1117 can include peripheral interface devices, such as a Universal Serial Bus (USB) interface, a PCMCIA (Personal Computer Memory Card International Association) interface, etc. Although a single communication interface 1117 is depicted in FIG. 11, multiple communication interfaces can also be employed.

The network link 1119 typically provides data communication through one or more networks to other data devices. For example, the network link 1119 may provide a connection through local network 1121 to a host computer 1123, which has connectivity to a network 1125 (e.g., a wide area network (WAN) or the global packet data communication network now commonly referred to as the "Internet") or to data equipment operated by a service provider. The local network 1121 and the network 1125 both use electrical, electromagnetic, or optical signals to convey information and instructions. The signals through the various networks and the signals on the network link 1119 and through the communication interface 1117, which communicate digital data with the computer system 1100, are exemplary forms of carrier waves bearing the information and instructions.

The computer system 1100 can send messages and receive data, including program code, through the network(s), the network link 1119, and the communication interface 1117. In the Internet example, a server (not shown) might transmit requested code belonging to an application program for implementing an embodiment of the invention through the network 1125, the local network 1121 and the communication interface 1117. The processor 1103 may execute the transmitted code while being received and/or store the code in the storage device 1109, or other non-volatile storage for later execution. In this manner, the computer system 1100 may obtain application code in the form of a carrier wave. Many parts of the application send code from the computer system 1100 to the host computer 1123 and to be executed on the host computer 1123. The host computer 1123 is not just for displaying data from the computer system 1100—it actively runs code sent by the computer system 1100 in order to interact with (1) the computer system 1100 (e.g., request more data) or (2) the host computer 1123 itself (e.g., sort or show/hide data in place without a round trip to the computer system 1100).

The term "computer-readable medium" as used herein refers to any medium that participates in providing instructions to the processor 1103 for execution. Such a medium may take many forms, including but not limited to computer-readable storage medium excluding transitory signals ((or non-transitory)—i.e., non-volatile media and volatile media), and transmission media. Non-volatile media include, for example, optical or magnetic disks, such as the storage device 1109. Volatile media include dynamic memory, such as main memory 1105. Transmission media include coaxial cables, copper wire and fiber optics, including the wires that comprise the bus 1101. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out at least part of the embodiments of the invention may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

Figure 12:
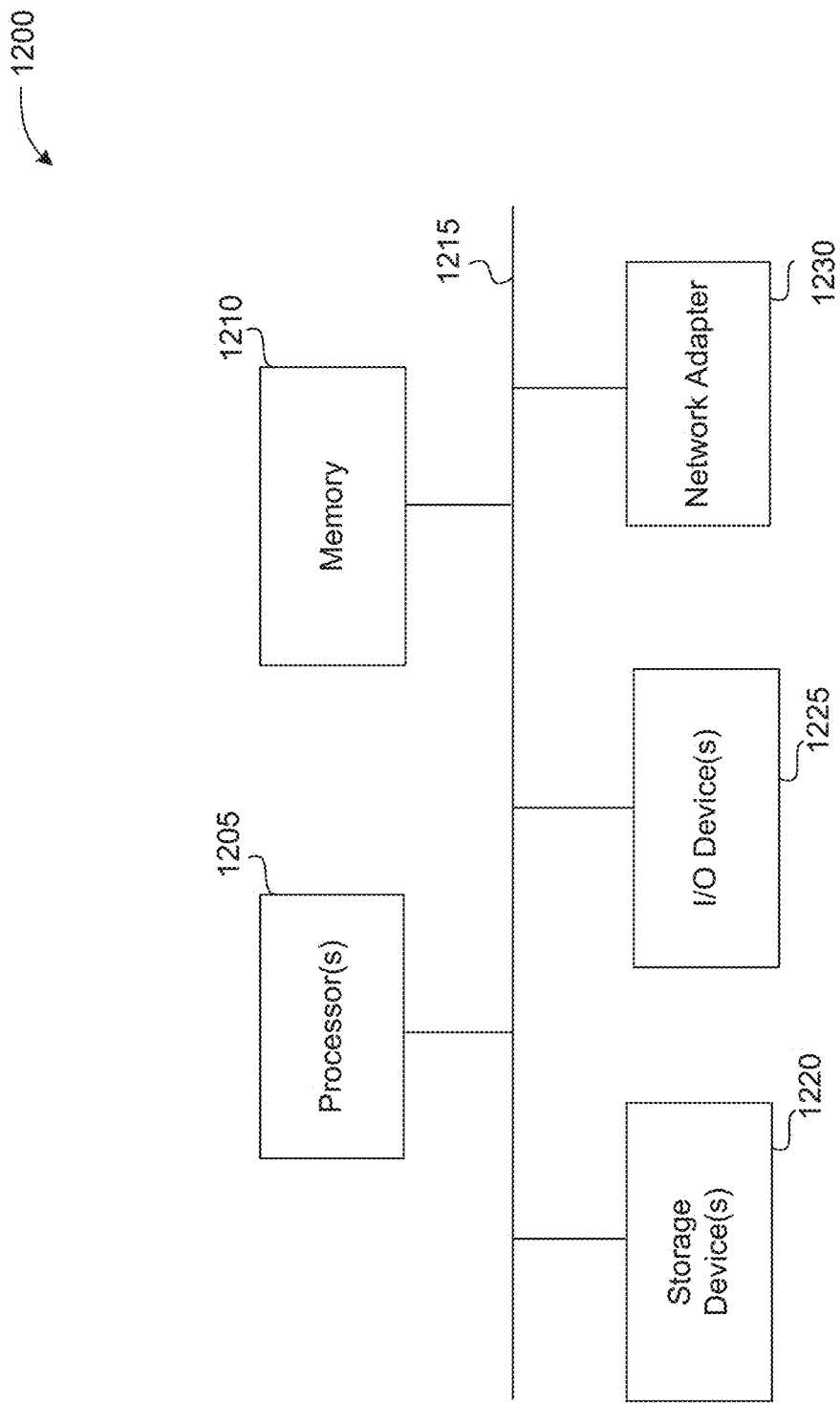
FIG. 12 is a diagram of a chip set that can be used to implement an embodiment of the invention.

FIG. 12 is a block diagram of a computer system as may be used to implement features of some embodiments of the disclosed technology. The computing system 1200 may be used to implement any of the entities, components or services depicted in the examples of FIGS. 1-11 (and any other components described in this specification). The computing system 1200 may include one or more central processing units ("processors") 1205, memory 1210, input/output devices 1225 (e.g., keyboard and pointing devices, display devices), storage devices 1220 (e.g., disk drives), and network adapters 1230 (e.g., network interfaces) that are connected to an interconnect 1215. The interconnect 1215 is illustrated as an abstraction that represents any one or more separate physical buses, point to point connections, or both connected by appropriate bridges, adapters, or controllers. The interconnect 1215, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The memory 1210 and storage devices 1220 are computer-readable storage media that may store instructions that implement at least portions of the described technology. In addition, the data structures and message structures may be stored or transmitted via a data transmission medium, such as a signal on a communications link. Various communications links may be used, such as the Internet, a local area network, a wide area network, or a point-to-point dial-up connection. Thus, computer readable media can include computer-readable storage media (e.g., "non-transitory" media) and computer-readable transmission media.

The instructions stored in memory 1210 can be implemented as software and/or firmware to program the processor(s) 1205 to carry out actions described above. In some embodiments, such software or firmware may be initially provided to the computing system 1200 by downloading it from a remote system through the computing system 1200 (e.g., via network adapter 1230).

REMARKS

The above description and drawings are illustrative and are not to be construed as limiting. Numerous specific details are described to provide a thorough understanding of the disclosure. However, in some instances, well-known details are not described in order to avoid obscuring the description. Further, various modifications may be made without deviating from the scope of the embodiments.

Reference in this specification to "one embodiment" or "an embodiment" means that a particular feature, structure, or characteristic described in connection with the embodiment is included in at least one embodiment of the disclosure. The appearances of such phrases in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Terms that are used to describe the disclosure are discussed below, or elsewhere in the specification, to provide additional guidance to the practitioner regarding the description of the disclosure. For convenience, some terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein, nor is any special significance to be placed upon whether or not a term is elaborated or discussed herein. Synonyms for some terms are provided. A recital of one or more synonyms does not exclude the use of other synonyms. The use of examples anywhere in this specification including examples of any term discussed herein is illustrative only, and is not intended to further limit the scope and meaning of the disclosure or of any exemplified term. Likewise, the disclosure is not limited to various embodiments given in this specification.

Those skilled in the art will appreciate that the logic illustrated in each of the flow diagrams discussed above may be altered in various ways. For example, the order of the logic may be rearranged, substeps may be performed in parallel, illustrated logic may be omitted, other logic may be included, etc.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

What is claimed is:

1. A computer-implemented method performed by a computer system, having a processor and a memory, for recommending customized treatment plans for patients, the method comprising:

receiving, by the processor, patient data including, for each of a plurality of patients, values for one or more of a plurality of healthcare attributes that apply to the patient and descriptions for one or more of a plurality of healthcare events involving the patient during a specific timeframe;

de-identifying, by the processor, the patient data with a unique patient key (UPK) for each of the plurality of patients;

joining, by the processor, the patient data of the plurality of patients longitudinally without linking any individual patient data to a personal identity;

generating, by the processor, consumer-friendly structured vocabularies that are mapped to standard medical terminology based on comparisons of semantic meanings by using historical search data provided by one or more search engines to generate ordered lists of health-related phrases that are mapped to the standard medical terminology, wherein the consumer-friendly structured vocabularies are distinct for different geographical regions;

receiving, by the processor, from a user device across a computer network, a search query including healthcare criteria involving at least one of the plurality of healthcare attributes described in consumer-friendly terms, wherein the criteria include a medical condition, a specific patient characteristic, and an inferred location based on an IP address of the user device;

identifying, by the processor, a group of UPKs associated with patient data that satisfies the healthcare criteria from the plurality of UPKs based on the values for the plurality of healthcare attributes;

clustering, by the processor, the group of UPKs into a plurality of clusters with respect to part or all of the plurality of healthcare events;

ranking, by the processor, the plurality of clusters based on sizes of the plurality of clusters;

for each of the clusters, ranking, by the processor, the plurality of healthcare events for the cluster based on the corresponding descriptions;

sending, by the processor, to the user device, a recommendation of treatment plans based on the ranking of the plurality of healthcare events for the highest-ranking cluster of UPKs; and causing display, on a display device of the user device, of query results including patient data from which the recommendation was generated while suppressing any personal identity of any of the plurality of patients, wherein the query results are based on a consumer-friendly structured vocabulary for a geographical region that includes the inferred location.

2. The computer-implemented method of claim 1, wherein each description for a healthcare event includes a weight and times of occurrence associated with the patient, the method further comprising:

determining a subset of the plurality of healthcare events that is less than the plurality of healthcare events for the group of patients based on the associated weights, wherein the clustering of the group of patients is performed with respect to the subset of healthcare events, and wherein for each of the clusters, the ranking of the plurality of healthcare events is based on the associated times of occurrence.

3. The computer-implemented method of claim 2, wherein the ranking of the plurality of healthcare events is based on occurrence of individual healthcare events and co-occurrence of two or more healthcare events.

4. The computer-implemented method of claim 2, wherein the weight is related to a significance of the healthcare event to the patient or a number of times the healthcare event occurred to the patient during the specific timeframe.

5. The computer-implemented method of claim 2, wherein the determining includes selecting a specific number of healthcare events with the largest sums of weights over the group of UPKs or applying principle component analysis.

6. The computer-implemented method of claim 1, further comprising:

sending to the user device an indication of availability of alternative treatment plans, which are related to the other clusters of patients and the corresponding rankings of the plurality of healthcare events.

7. The computer-implemented method of claim 1, wherein the healthcare attributes include gender, age, location, medical diagnosis, medical history, medical system utilization, insurance plan, or insurance plan utilization.

8. The computer-implemented method of claim 7, wherein the medical diagnosis is related to comorbidities.

9. The computer-implemented method of claim 1, where each healthcare event is associated with a healthcare provider, a healthcare facility, a healthcare procedure, or a cost.

10. The computer-implemented method of claim 9, further comprising computing a sum of costs associated with part or all of the plurality of healthcare events for each patient in the highest-ranking cluster of patients, wherein the recommendation includes an aggregate or a distribution of the sums.

11. The computer-implemented method of claim 1, wherein the one of the plurality of healthcare attributes is provider type, the method further comprising:

for the highest-ranking cluster of UPKs patients, identifying a group of providers associated with the plurality of healthcare events, wherein the recommendation includes part or all of the group of providers.

12. The computer-implemented method of claim 11, further comprising:

for the highest-ranking cluster of patients, extending the group of providers with additional providers affiliated with the providers in the group, wherein the affiliation is based on patient referral, patient sharing, or facility sharing, and wherein the recommendation includes the extended group of providers.

13. The computer-implemented method of claim 1 wherein the one of the plurality of healthcare attributes is facility type, further comprising:

for the highest-ranking cluster of patients, identifying a group of facilities associated with the plurality of healthcare events, wherein the recommendation includes part or all of the group of facilities.

14. A system for recommending customized treatment plans for patients, the system comprising:

a processor; and a memory coupled to the processor, wherein the memory includes instructions which, when executed by the processor, cause the system to:

maintain a database of patient data including, for each of a plurality of patients, values for one or more of a plurality of healthcare attributes that apply to the patient and descriptions for one or more of a plurality of healthcare events involving the patient during a specific timeframe;

de-identify the patient data with a unique patient key (UPK) for each of the plurality of patients;

join the patient data of the plurality of patients longitudinally without linking any individual patient data to a personal identity;

generate consumer-friendly structured vocabularies that are mapped to standard medical terminology based on comparisons of semantic meanings by using historical search data provided by one or more search engines to generate ordered lists of health-related phrases that are mapped to the standard medical terminology, wherein the consumer-friendly structured vocabularies are distinct for different geographical regions;

receive from a user device, across a computer network, a search query including healthcare criteria involving at least one of the plurality of healthcare attributes described in consumer-friendly terms wherein the criteria include a medical condition, a specific patient characteristic, and an inferred location based on an IP address of the user device;

identify a group of UPKs associated with patient data that satisfies the healthcare criteria from the plurality of patients based on the values for the plurality of healthcare attributes;

classify the group of UPKs into one or more classes with respect to part or all of the plurality of healthcare events;

rank the one or more classes;

score, for each of the classes, the plurality of healthcare events for the class based on the corresponding descriptions;

transmit to the user device a recommendation of treatment plans based on the scoring of the plurality of healthcare events for the highest-ranking class of patients; and cause display, on a display device of the user device, of query results including patient data from which the recommendation was generated while suppressing any personal identity of any of the plurality of patients, wherein the query results are based on a consumer-friendly structured vocabulary for a geographical region that includes the inferred location.

15. The system of claim 14, wherein the ranking of the one or more classes is performed based on sizes of the one or more classes.

16. The system of claim 14,
wherein each description for a healthcare event includes a weight and times of occurrence associated with the patient,
wherein the system is further caused to:
determine a subset of the plurality of healthcare events that is less than the plurality of healthcare events for the group of UPKs based on the associated weights,
classify the group of UPKs with respect to the subset of healthcare events, and
for each of the classes, score the plurality of healthcare events based on the associated times of occurrence.

17. The system of claim 14, wherein the system is further caused to transmit an indication of availability of alternative treatment plans to a user interface, which is related to the other classes of patients and the corresponding scorings of the plurality of healthcare events.

18. The system of claim 14, wherein the healthcare attributes include gender, age, location, medical diagnosis, medical history, medical system utilization, insurance plan, or insurance plan utilization.

19. The system of claim 14, where each healthcare event is associated with a healthcare provider, a healthcare facility, a healthcare procedure, or a cost.

20. A non-transitory computer-readable medium having computer-executable instructions adapted to cause a computer system to perform a method of recommending customized treatment plans for patients, the method comprising:

receiving patient data including, for each of a plurality of patients, values for one or more of a plurality of healthcare attributes that apply to the patient and descriptions for one or more of a plurality of healthcare events involving the patient during a specific timeframe;

wherein each description for a healthcare event includes a weight and times of occurrence associated with the patient;

de-identifying the patient data with a unique patient key (UPK) for each of the plurality of patients;

joining the patient data of the plurality of patients longitudinally without linking any individual patient data to a personal identity;

generating consumer-friendly structured vocabularies that are mapped to standard medical terminology based on comparisons of semantic meanings by using historical search data provided by one or more search engines to generate ordered lists of health-related phrases that are mapped to the standard medical terminology, wherein the consumer-friendly structured vocabularies are distinct for different geographical regions;

receiving from a user device across a computer network, a search query including healthcare criteria involving at least one of the plurality of healthcare attributes described in consumer-friendly terms, wherein the criteria include a medical condition, a specific patient characteristic, and an inferred location based on an IP address of the user device;

identifying a group of UPKs associated with patient data that satisfies the healthcare criteria from the plurality of UPKs based on the values for the plurality of healthcare attributes;

determining a subset of the plurality of healthcare events that is less than the plurality of healthcare events for the group of UPKs based on the associated weights, clustering the group of UPKs into a plurality of clusters based on the descriptions for the subset of healthcare events;

ranking the plurality of clusters based on sizes of the plurality of clusters;

for each of the clusters, ranking the plurality of healthcare events for the cluster based on the associated times of occurrence;

sending to the user device a recommendation of treatment plans based on the ranking of the plurality of healthcare events for the highest-ranking cluster of patients; and causing display, on a display device of the user device, of query results including patient data from which the recommendation was generated while suppressing any personal identity of any of the plurality of patients, wherein the query results are based on a consumer-friendly structured vocabulary for a geographical region that includes the inferred location.

21. A computer-implemented method performed by a server computer for communicating personalized healthcare data that is created based on existing patient data, the method comprising:

collecting, for each of a plurality of patients, patient data including values for one or more of a plurality of healthcare attributes and descriptions of one or more of a plurality of healthcare events,
wherein each description for a healthcare event includes a weight and time of occurrence, and
wherein the weight is related to a significance of the healthcare event to the patient or an amount of times that the healthcare event occurred to the patient during a specific timeframe;

de-identifying, for each of the plurality of patients, the patient data with a unique patient key (UPK);

joining the patient data of the plurality of patients longitudinally without linking to a personal identity of any of the plurality of patients;

generating a structured vocabulary that maps non-standard consumer friendly terms to standard medical terminology based on comparisons of semantic meanings by using historical search data provided by one or more search engines to generate an ordered list of health-related terms that are mapped to the standard medical terminology, receiving a search query from a user device over a computer network,
  wherein the search query includes criteria involving the plurality of healthcare attributes described in non-standard consumer-friendly terms;

identifying a group of UPKs associated with patient data that satisfies the criteria based on the values for the plurality of healthcare attributes;

clustering the group of UPKs into a plurality of clusters with respect to the plurality of healthcare events;

ranking the plurality of clusters based on sizes of the plurality of clusters;

for each of the clusters, ranking the plurality of healthcare events based on an occurrence of individual healthcare events and co-occurrence of two or more healthcare events;

sending, over a computer network to the user device, query results including personalized healthcare data that is generated based on the ranking of the plurality of healthcare events for the highest-ranking cluster of UPKs,
  wherein the query results include an indication of alternative personalized healthcare data corresponding to the remaining clusters of UPKs other than the highest-ranking cluster of UPKs; and causing display, on a display device of the user device, of the query results including patient data from which the personalized healthcare data was generated while suppressing any personal identity of any of the plurality of patients.

* * * * *